(12) United States Patent
Fortin et al.

(10) Patent No.: US 10,359,354 B2
(45) Date of Patent: Jul. 23, 2019

(54) CHIP ASSEMBLY, FLOW CELL AND FLOW CYTOMETER FOR CHARACTERIZING PARTICLES

(71) Applicant: HANDYEM INC., Quebec, Quebec (CA)

(72) Inventors: Michel Fortin, Quebec (CA); Alain Chandonnet, Quebec (CA); Dany Nolet, L'Ancienne-Lorette (CA)

(73) Assignee: AZURE BIOSYSTEMS, INC., Dublin, CA (US)

( * ) Notice: Subject to any disclaimer, the term of this patent is extended or adjusted under 35 U.S.C. 154(b) by 0 days.

(21) Appl. No.: 15/106,056

(22) PCT Filed: Dec. 18, 2013

(86) PCT No.: PCT/CA2013/001071
§ 371 (c)(1),
(2) Date: Jun. 17, 2016

(87) PCT Pub. No.: WO2015/089621
PCT Pub. Date: Jun. 25, 2015

(65) Prior Publication Data
US 2016/0320288 A1    Nov. 3, 2016

(51) Int. Cl.
*G01N 15/14*    (2006.01)
*G01N 21/64*    (2006.01)
(Continued)

(52) U.S. Cl.
CPC ......... *G01N 15/1436* (2013.01); *G01N 21/05* (2013.01); *G01N 21/53* (2013.01);
(Continued)

(58) Field of Classification Search
CPC ......... G01N 2015/149; G01N 15/1459; G01N 15/1475; G01N 15/1434; G01N 15/1484;
(Continued)

(56) References Cited

U.S. PATENT DOCUMENTS 6,664,104 B2 * 12/2003 Pourahmadi ........... C12M 47/06
422/547
8,220,494 B2 * 7/2012 Studer ................. G06F 17/5018
137/833

(Continued)

*Primary Examiner* — Taeho Jo
(74) *Attorney, Agent, or Firm* — Brouillette Legal Inc.; Robert Brouillette

(57) ABSTRACT

The present relates to a chip assembly, a flow cell and a cytometer for characterizing particles in a sample solution. The chip assembly comprises a pair of chips, at least one of the chip defining on its inner surface at least two channels, the two channels defining therebetween a common intersecting area. Each channel is adapted for receiving one or more optical fibers. The chips define a through-hole extending throughout the chip assembly in a transverse direction relative to the channels and passing through the common intersecting area. The flow cell comprises the chip assembly, an excitation fiber and at least one collection fiber extending through respective channels; the collection fiber for collecting light scattered or emitted by particles flowing through the through-hole and excited by an excitation light transported by the excitation fiber. The flow cytometer comprises a light source for generating the excitation light and the flow cell.

19 Claims, 15 Drawing Sheets

(51) Int. Cl.
  *G01N 21/05*  (2006.01)
  *G01N 21/53*  (2006.01)
  *G01N 21/47*  (2006.01)
  *G01N 15/10*  (2006.01)

(52) U.S. Cl.
  CPC ....... *G01N 21/645* (2013.01); *G01N 21/6428*
  (2013.01); *G01N 15/1459* (2013.01); *G01N*
  *2015/1006* (2013.01); *G01N 2021/4707*
  (2013.01); *G01N 2021/6439* (2013.01); *G01N*
  *2021/6482* (2013.01); *G01N 2201/08*
  (2013.01)

(58) Field of Classification Search
  CPC ......... G01N 2015/0065; G01N 33/587; G01N
  15/1463; G01N 21/05; G01N 21/6458;
  G01N 21/75; G01N 2201/08; G01N
  21/53; G01N 21/6428; G01N 21/645;
  G01N 2015/1006; G01N 2021/4707;
  G01N 2021/6439; G01N 2021/6482
  USPC ...................................................... 250/458.1
  See application file for complete search history.

(56) References Cited

U.S. PATENT DOCUMENTS

| | | | |
|---|---|---|---|
| 2003/0054558 A1* | 3/2003 | Kurabayashi ...... G01N 15/1404 436/63 |
| 2004/0080744 A1* | 4/2004 | Hobbs ............... B01L 3/502715 356/246 |
| 2004/0209354 A1* | 10/2004 | Mathies .................... B01F 5/10 435/287.2 |
| 2004/0224002 A1* | 11/2004 | Fishman .............. A61N 1/0543 424/423 |
| 2005/0252773 A1* | 11/2005 | McBride ................. C12Q 1/68 204/450 |
| 2006/0177348 A1* | 8/2006 | Yasuda ............. B01L 3/502715 422/73 |
| 2007/0041009 A1* | 2/2007 | Iwano .................... G01N 30/74 356/246 |
| 2007/0047868 A1* | 3/2007 | Beaulieu ............ G01N 15/1459 385/12 |
| 2008/0010821 A1* | 1/2008 | Padmanabhan ......... G01F 1/684 29/842 |
| 2008/0070311 A1* | 3/2008 | Li ...................... G01N 15/1459 436/63 |
| 2008/0176290 A1* | 7/2008 | Joseph .................. C12Q 1/686 435/91.2 |
| 2009/0014360 A1* | 1/2009 | Toner ................. B01D 21/0087 209/208 |
| 2009/0051901 A1* | 2/2009 | Shen ................ B29D 11/00365 356/73 |
| 2009/0311717 A1* | 12/2009 | De Sonneville .. B01L 3/502715 435/7.2 |
| 2010/0230613 A1* | 9/2010 | Pieprzyk ........... B01L 3/502738 250/459.1 |
| 2010/0247384 A1* | 9/2010 | Takayama ......... B01L 3/50273 422/504 |
| 2010/0277722 A1* | 11/2010 | Kraiczek ............. B81C 1/00071 356/244 |
| 2011/0003303 A1* | 1/2011 | Pagano ............. B01L 3/502761 435/6.19 |
| 2011/0005932 A1* | 1/2011 | Jovanovich ...... G01N 35/00029 204/453 |
| 2011/0089328 A1* | 4/2011 | Li ...................... B01L 3/50273 250/364 |
| 2011/0174623 A1* | 7/2011 | Harrold .................. B01D 57/02 204/547 |
| 2011/0291025 A1* | 12/2011 | Fortin ................ G01N 15/1436 250/458.1 |
| 2012/0138461 A1* | 6/2012 | Sugiyama ......... B01L 3/502707 204/451 |
| 2012/0152006 A1* | 6/2012 | Aeppli ............. B01L 3/502715 73/64.56 |
| 2012/0252704 A1* | 10/2012 | Jaffe ........................ G01J 3/10 506/39 |
| 2012/0307244 A1* | 12/2012 | Sharpe .............. G01N 15/1012 356/338 |
| 2013/0005606 A1* | 1/2013 | Chakravarty ........ G01N 21/253 506/9 |
| 2013/0104632 A1* | 5/2013 | Lin .................... G01N 15/1459 73/61.59 |
| 2013/0315782 A1* | 11/2013 | Huang ................... G01N 27/00 422/69 |
| 2013/0342837 A1* | 12/2013 | Chandonnet ....... G01N 15/1436 356/337 |
| 2015/0204816 A1* | 7/2015 | Bancaud .......... G01N 27/44791 204/454 |
| 2016/0184789 A1* | 6/2016 | Takagi ................ B01J 19/0093 422/502 |

* cited by examiner

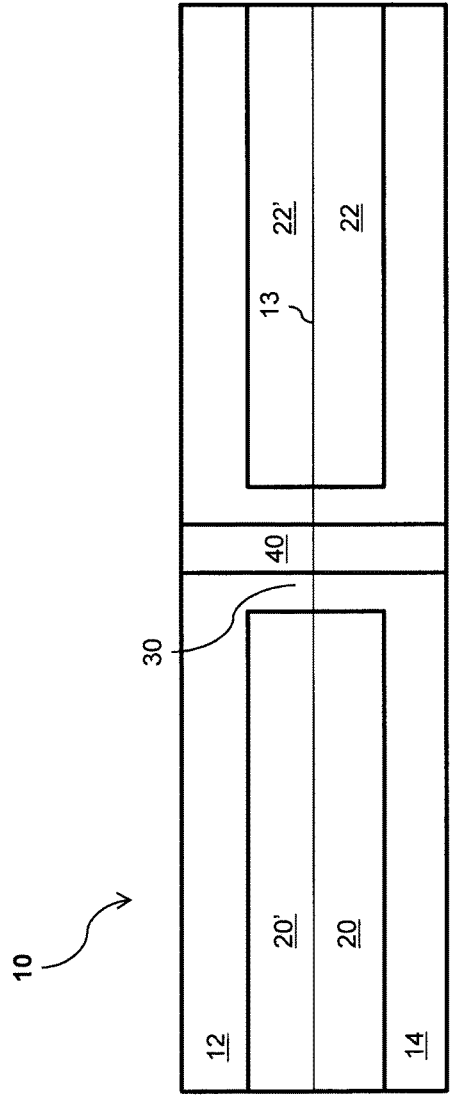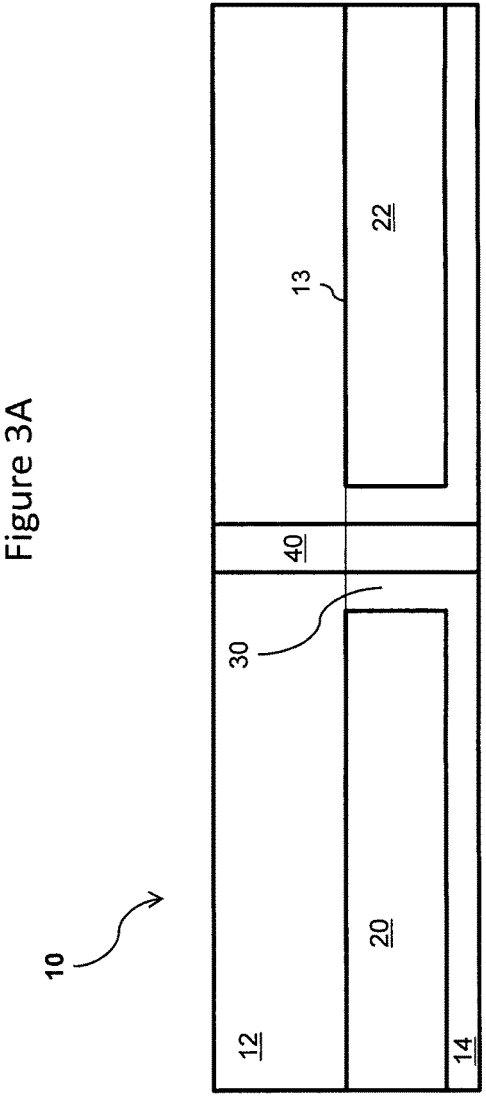

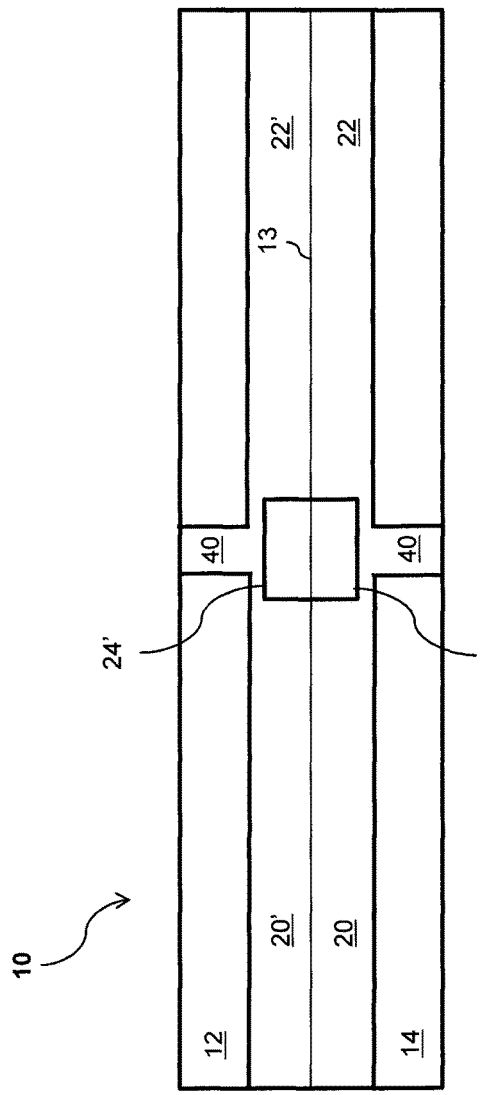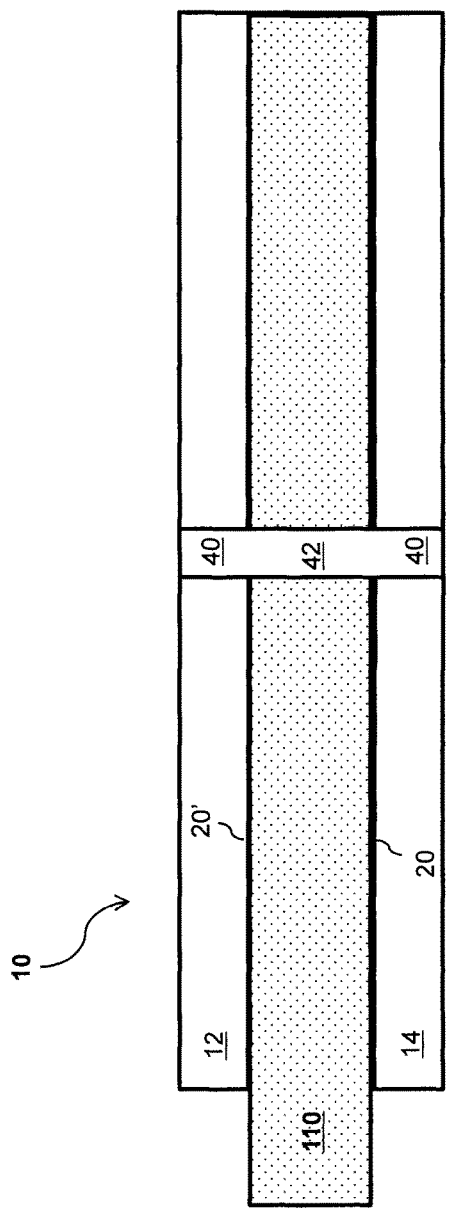

CHIP ASSEMBLY, FLOW CELL AND FLOW CYTOMETER FOR CHARACTERIZING PARTICLES

TECHNICAL FIELD

The present disclosure relates to the field of particles characterization in the context of flow cytometry. More specifically, the present disclosure relates to a chip assembly and a flow cell for characterizing particles.

BACKGROUND

A flow cell is an apparatus for characterization of particles suspended in a sample solution. Particles sizes are generally in the range of ~0.5-40 µm. Particles are analyzed one-by-one with a typical count rate in the range of a few to thousand particles per second. Depending on its configuration, a flow cell could allow estimating different information about the particles such as presence, concentration, dimension, shape, vitality (in the case of cells), types of biological cells, structural and/or functional information, etc. Using a flow cell for sorting particles of different types in a heterogeneous solution is also possible. An example of a flow cell is described in International Application no PCT/CA2013/000565 to Alain Chandonnet, Michel Fortin and Dany Nolet, filed on Jun. 12, 2013, the disclosure of which is incorporated by reference herein.

Flow cytometers, which incorporate different configurations of flow cells, have been developed over the last 40 years. In general, a light source (i.e. a laser) emitting a light beam is focused on a fluid stream in the flow cell. The fluid flows at a predetermined rate in a capillary tube of the flow cell. Particles in the fluid stream cross the light during a brief interval of time, hence forming a short burst of temporal scattered and fluorescence light. A collection optics assembly, localized near or around the region where light and fluid intersect collects light emitted and/or scattered by the particles. The collected light is spectrally separated by a detection subassembly system, including for example various optical filters, and then received by detectors. Optical signal parameters of the collected light are measured by the detectors, and are processed by a computational system and/or electronic components.

In one particular configuration, the flow cell includes an excitation fiber for transporting an excitation light generated by the light source. The excitation fiber comprises a passageway, for allowing the fluid to flow through the excitation fiber and thus allowing the particles in the flow to interact with the excitation light. The flow cell also includes at least one collection fiber for collecting light scattered or emitted by the particles flowing through the passageway and excited by the excitation light. In this particular configuration, the use of a capillary tube for fluid injection into the passageway of the excitation fiber is necessary to avoid compromising the characteristics of the collection fiber(s) and the overall performances of the flow cell.

Furthermore, immersion oil is generally used for index matching between the excitation fiber, collection fiber(s) and the capillary tube, to minimize stray light due to numerous optical interfaces and block generation of auto-fluorescence and spontaneous Raman scattering which can limit sensitivity. The immersion oil can be removed easily if in contact with water (for instance during rinsing of the capillary tube), rendering the flow cell unusable.

Although the capillary tube allows maintaining the characteristics of the collection fiber(s) and the overall performances of the flow cell, its use has several drawbacks. First, because the capillary tube is relatively small in diameter and have a certain length, it can be clogged by the particles in the sample, thus becoming inoperative. Some mechanisms permit rinsing the capillary tube, but again, due to its relative size and length, pressure of the rinsing liquid must be maintained within safe limits. Furthermore, the use of the capillary tube together with the excitation fiber and the collection fiber(s) require precise relative adjustment to ensure proper functioning of the flow cell. As the capillary tube, excitation fiber and collection fiber(s) are small components, replacement of a capillary tube in the flow cell is not a simple task which can be performed quickly, but rather requires concentration and precision. Immersion oil for epifluorescence microscope must be used between the capillary tube and the oil without excess (~nl). The capillary tube must be glued at both extremities without blocking the entrances. Care must be taken during the assembling process because of the fragility of the capillary tube. Also, even immersion oil for epifluorescence microscopy can generate autofluorescence and spontaneous raman scattering.

There is therefore a need for an improved flow cell for characterizing particles in a solution, to mitigate or eliminate these drawbacks.

SUMMARY

According to an aspect, the present disclosure relates to a chip assembly for use in a flow cell. The chip assembly comprises a pair of chips. At least one of the chip defines on its inner surface at least two channels, the two channels defining therebetween a common intersecting area. Each channel is adapted for receiving one or more optical fibers. The pair of chips further defines a through-hole extending throughout the chip assembly in a transverse direction relative to the channels, such that the through-hole passes through the common intersecting area.

In another aspect, the present disclosure relates to a flow cell for characterizing particles in a sample solution. The flow cell comprises the aforementioned chip assembly. The flow cell further comprises one or more excitation fibers extending through one of the channels defined by the chip assembly. Each of the one or more excitation fibers has at least one core for transporting an excitation light. The flow cell also comprises at least one collection fiber extending through another one of the channels defined by the chip assembly. The at least one collection fiber collects light scattered or emitted by the particles flowing through the through-hole and excited by the excitation light.

In still another aspect, the present disclosure relates to a flow cytometer for characterizing particles in a sample solution. The flow cytometer comprises at least one light source for generating an excitation light. The flow cytometer further comprises the aforementioned flow cell, wherein the at least one core of each of the one or more excitation fibers transports the excitation light.

The foregoing and other features of the present chip assembly and flow cell will become more apparent upon reading of the following non-restrictive description of illustrative embodiments thereof, given by way of example only with references to the accompanying drawings.

BRIEF DESCRIPTION OF THE DRAWINGS

Embodiments of the disclosure will be described by way of examples only, with reference to the accompanying drawings, in which:

FIGS. 3A and 3B are a cross-sectional elevation view of the chip assembly of FIG. 1 with channels and a through-hole, according to a non-restrictive illustrative embodiment;

FIG. 6A is a cross-sectional elevation view of the chip assembly of FIG. 1 with channels and a through-hole, according to a non-restrictive illustrative embodiment;

FIG. 6B is view of the chip assembly of FIG. 6A with an excitation fiber having a passageway, according to a non-restrictive illustrative embodiment;

DETAILED DESCRIPTION

The following terminology is used throughout the present disclosure, and is meant to be interpreted as follows:

Sample solution: fluid containing suspended particles.

Flow cell: component used in conjunction with a cytometer for characterizing particles in suspension in the sample solution, the component relying on principles of light propagation, light scattering and/or fluorescence.

Light scattering: physical process by which light deviates from its path after interacting with a perturbation of the medium it is propagating in, such as a variation of the index of refraction, an interface, etc.

Fluorescence: light emitted after absorption of incident light by a medium or particle, where the wavelength of the light emitted is longer (lower energy) than the wavelength of the incident light (higher energy).

Excitation zone: intersection of an excitation light and the sample solution.

Excitation fiber: optical fiber transporting the excitation light from a light source to the excitation zone.

Collection fiber: optical fiber located in proximity of the excitation zone, to collect light scattered or emitted by the particles in the excitation zone.

Through-hole: conduit extending through a chip assembly for passage of the sample solution.

Passageway: conduit extending through a fiber for passage of the sample solution.

As previously discussed, use of a capillary tube in a flow cell causes several drawbacks. Thus, avoiding the use of a capillary tube in developing and implementing a flow cell would have many advantages from a fluidic-optic point of view. For instance, there would be less pressure restrictions into the flow cell for fluid insertion, the flow cell could be used in a pull direction instead of a push direction, unclogging of the fluid through-hole would be easier, and there would be less swept/dead volume for the fluid circulation. Additionally, the flow cell could be rinsed at a higher flow rate, for increasing the number of samples which could be analyzed in a day.

The present description discloses a chip assembly and a flow cell using the present chip assembly for characterizing particles in a sample solution. The present description also relates to an apparatus, such as for example a flow cytometer, using the present flow cell, and adapted to characterize particles in a sample solution.

Chip Assembly

The present chip assembly is composed of two complementary chips, assembled one above the other so as to form a building block of a flow cell.

Figure 1:
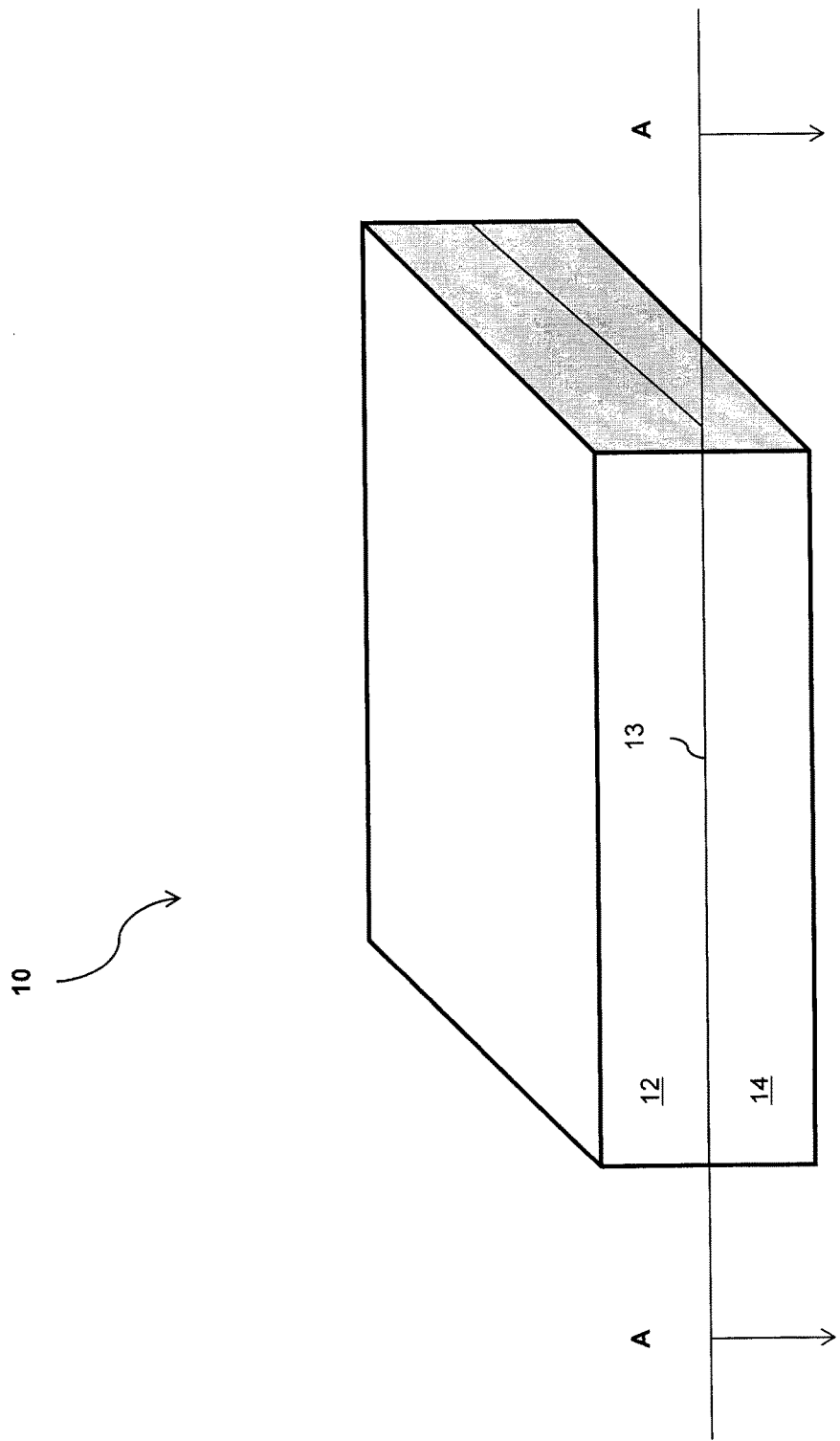
FIG. 1 is a perspective view of a chip assembly, according to a non-restrictive illustrative embodiment.

Reference is now made to FIG. 1, which represents a perspective view of a chip assembly 10 having a parallelepiped form. The chip assembly 10 is composed of an upper chip 12 and a lower chip 14, assembled one above the other. The chip assembly 10 represented in FIG. 1 is for illustration purposes only. The parallelepiped form is well suited for assembly in a flow cell, but other forms may be used if appropriate. Furthermore, the dimensions of the chip assembly 10 (e.g. length, width and height for the parallelepiped form) are adapted for forming a flow cell.

At least one of the two chips 12 and 14 comprises at least two channels on its inner surface 13 for receiving optical fibers. The channels extend from a periphery of the inner surface 13 towards a common intersecting area. One optical fiber can be received by each channel. The chip assembly 10 also comprises a through-hole extending throughout the chip assembly 10 in a transverse direction relative to the channels, such that the through-hole passes through the common intersecting area. The through-hole extends throughout each chip 12 and 14 in such a manner that when the chips 12 and 14 are assembled to form the chip assembly 10, the through-holes of the chips 12 and 14 are aligned so as to form the through-hole of the chip assembly 10.

Chip Assembly for Receiving an Excitation Fiber without a Passageway

Figure 2:
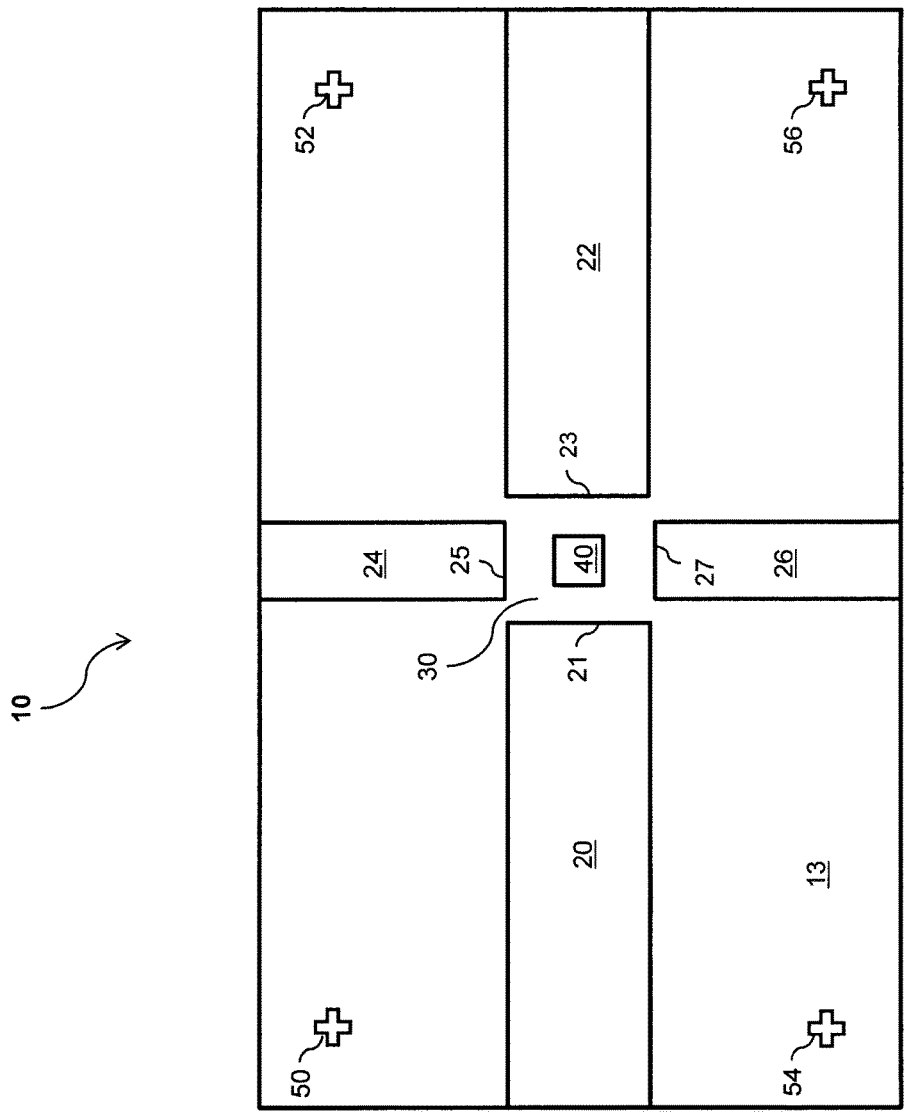
FIG. 2 is a cross-sectional view of the chip assembly of FIG. 1 with channels and a through-hole as seen along line A-A of FIG. 1, according to a non-restrictive illustrative embodiment.

Reference is now concurrently made to FIGS. 2, 3A and 3B, which represent a cross-sectional view along line A-A of FIG. 1 and two cross-sectional elevation views of the chip assembly 10 with the channels and the through-hole.

For illustration purposes, four channels 20, 22, 24, 26 are represented on the inner surface 13 of the lower chip 14 of the chip assembly 10. FIG. 3A illustrates a configuration where the channels (e.g. 20, 20' and 22, 22') are present on the inner surface 13 of both the lower chip 14 and the upper chip 12. FIG. 3B illustrates an alternative configuration where the channels (e.g. 20 and 22) are present only on the inner surface 13 of the lower chip 14. In still another alternative not represented in the Figures, the channels may be present only on the inner surface 13 of the upper chip 12.

Each channel (e.g. 20) extends from one extremity of the inner surface 13 of the chip (12 and/or 14) towards the intersecting area 30. The channels do not extend into the intersecting area 30, since the excitation fiber to be received in one of the channels does not have a passageway to be aligned with the through-hole 40 of the chip assembly 10. The shape of the channels is adapted to the shape of the optical fibers to be received (for example, a parallelepiped shape for receiving a fiber having a rectangular, square or circular cross section, a cylindrical shape for receiving a fiber having a circular cross section). The optical fibers have not been represented in FIGS. 2, 3A and 3B for simplification purposes. In the embodiment schematically represented in FIG. 2, each channel defines a rectangular shape on the inner surface 13. The cross-sectional shape of a channel may consist of a rectangle, half a circle, half an ellipse, or of any shape suitable for receiving and aligning the optical fibers with respect to the intersecting area 30. Each channel may have a different shape, or some of the channels may have a similar shape.

The common intersecting area 30 is a region of the chip assembly 10, where all the channels converge. The common intersecting area 30 defines a volume of chip material, in contact with each terminating sections (e.g. 21, 23, 25, 27) of the channels (e.g. 20, 22, 24, 26).

As shown in FIG. 2, the channels may consist of two pairs of channels: a first pair comprising channels 20 and 22 (which are substantially aligned with each other), and a second pair comprising channels 24 and 26 (which are substantially aligned with each other). Furthermore, the two pairs of channels could substantially be perpendicular to each other. The common intersecting area 30 may define a substantially parallelepiped form. It is possible to design the length of the channels, such that, the common intersecting area 30 defines a volume of chip material corresponding to a cube. Although two pairs of perpendicular channels are shown in FIG. 2, the present chip assembly and flow cell are not limited to such an implementation. The present chip assembly and flow cell can use any variant of channels which define an intersecting area and volume of chip material suitable for optical measurements of any fluid sample passing within the chip assembly 10 and flow cell through the through-hole 40, such as for example: channels for allowing multiple concurrent excitation fibers, collection fibers located with respect to the intersecting area for collecting forward light scattering, backward light scattering, side light scattering, etc.

The through-hole 40 extends throughout the chips 12 and 14 and more particularly through the common intersecting area 30. The through-hole 40 may have any alternative form adapted for use in a flow cell, for example a square or rectangle shape, a cylindrical shape, etc. The through-hole 40 is represented substantially in the center of the chip assembly 10, but the through-hole 40 could be located anywhere on the chips 12 and 14, as long as it is in the intersecting area 30.

Figure 4:
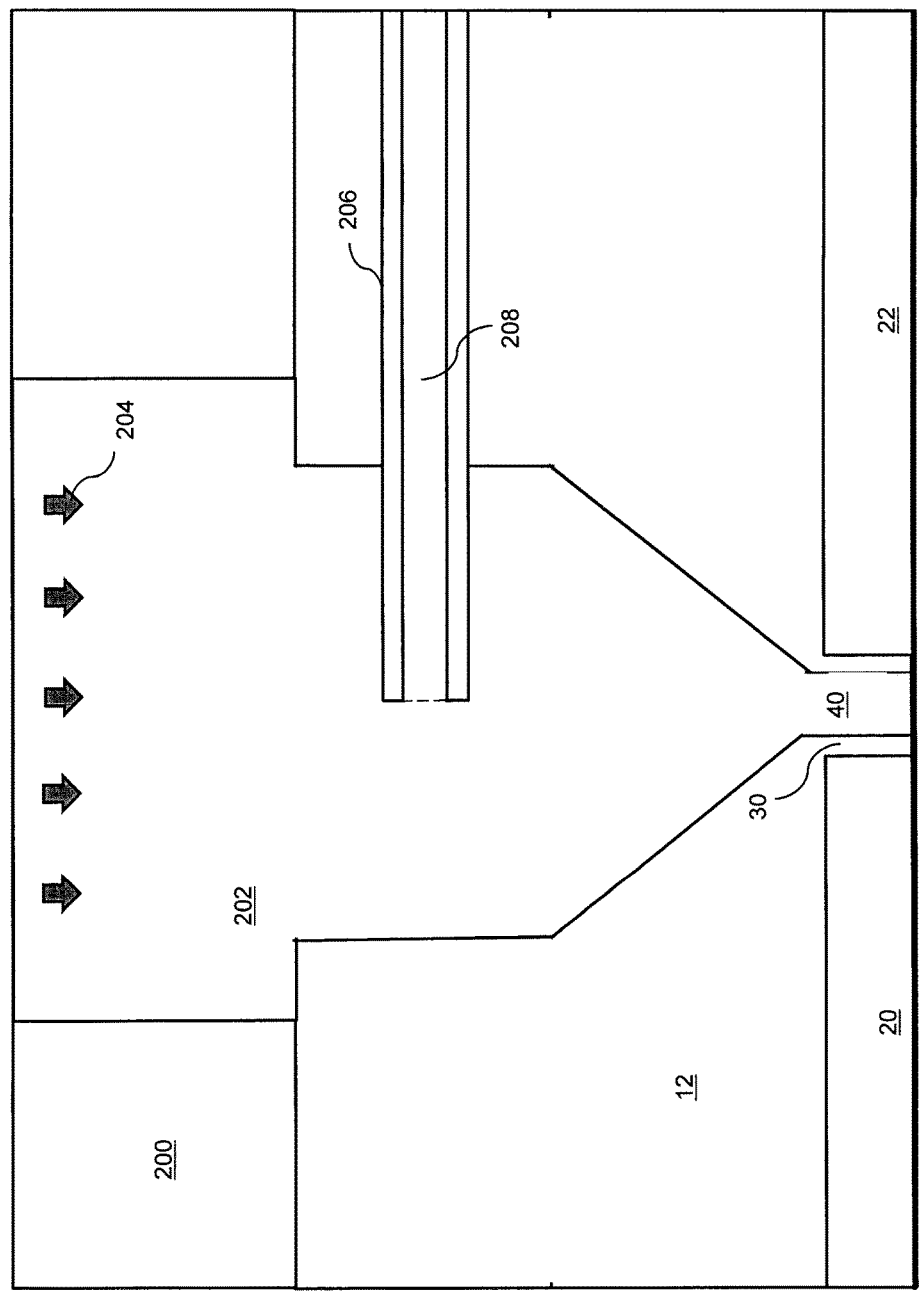
FIG. 4 is a cross-sectional, schematic view of a variant of the chip assembly of FIG. 1, configured for hydrodynamic focusing generation.

FIG. 4 is a cross-sectional, schematic view of a variant of the chip assembly of FIG. 1, configured for hydrodynamic focusing generation. A top plate 200 (described in more details hereinbelow) is placed on top of the chip 12. The top plate 200 comprises a funnel-shaped void 202, which is for example 1000 µm wide, positioned above the through-hole 40 and tapering throughout a depth of the chip 12 to arrive substantially at a width of the through-hole 40, for example 100 µm wide, above the level of the channels 20 and 22. A sheath fluid 204 is pumped into the void 202 and forms a stream flowing toward the through-hole 40. A tubing 206 brings a sample fluid 208 injected centrally within the stream of sheath fluid 204. The flow stream coming from the tubing 206, which has a substantially lower flow rate than sheath fluid 204, is then pinched in the through-hole 40 by the sheath fluid 204. This creates a single file of particles suspended in the sample fluid 208 at the center of the through-hole 40. A symmetrical arrangement (not shown) of the chip 14 may broaden the width of the through-hole 40 downstream of the channels 20 and 22.

Returning to FIG. 2, for ease of alignment of the chips 12 and 14, alignment guides 50, 52, 54 and 56, for example crosses, may optionally be provided on their inner surfaces 13. For example, male guides 50 and 56 may protrude from the surface of the chip 12 and mate with female guides 50 and 56 dug into the surface of the chip 14. At the same time, female guides 52 and 54 may be dug into the surface of the chip 12 and mate with male guides 52 and 54 protruding from the surface of the chip 14. Alternatively, the chips 12 and 14 may be identical and construction of the chip assembly 10 can be made by placing the two identical chips facing each other; in that case, male guides 52 and 54 of one chip respectively mate with female guides 50 and 56 of the opposite chip. The use of the alignment guides 50-56 facilitates inter-chip indexation when making the chip assembly 10. Various numbers, shapes and configurations of alignment guides are contemplated and the four (4) crosses as shown are provided for illustration purposes without limiting the present disclosure.

The chip assembly 10 the upper 12 and lower 14 chips) may be made of various kinds of glasses adapted for use in a flow cell. In particular, since the common intersecting area 30 is excited by an excitation light when assembled in a flow cell, auto-fluorescence and spontaneous Raman and Rayleigh scattering are minimized. Thus, fused silica and quartz are particularly appropriate materials for making the chip assembly 10.

When the chip assembly 10 comprises only one chip (e.g. 14) with channels as illustrated in FIG. 3B, the chip (e.g. 12) without channels may be made of a material different from the chip with channels. For instance, the chip without channels may be made of plastic, for providing a better sealing of the optical components from a fluid flowing through the through-hole 40.

There are several advantages in using the present chip assembly in replacement of the traditional flow cell using a capillary tube: the present chip assembly reduces the need to align each component (excitation fiber(s), collection fiber(s), capillary tube), the assembly is easier and has a better repeatability, it is easier to modify the optical characteristics of the flow cell to be application specific, and it is cheaper to produce. Using the chip assembly allows to rapidly and precisely locate each optical fiber into the flow cell, for example within less than a 10 µm range. Additionally, the chip assembly can be used for assembling a flow cell without the use of glue, allowing disassembly and rebuild of the flow cell.

In addition to the aforementioned advantages, the present chip assembly also allows fast and simple integration of a microfluidic chip on an exterior surface of one of the chips. Thus, the chip assembly can include not only the channels to align the excitation and collection fiber(s), but also define the fluid through-hole, and include a microfluidic chip to treat/filter the fluid sample prior to passing through the fluid through-hole.

Chip Assembly for Receiving an Excitation Fiber with a Passageway

Figure 5:
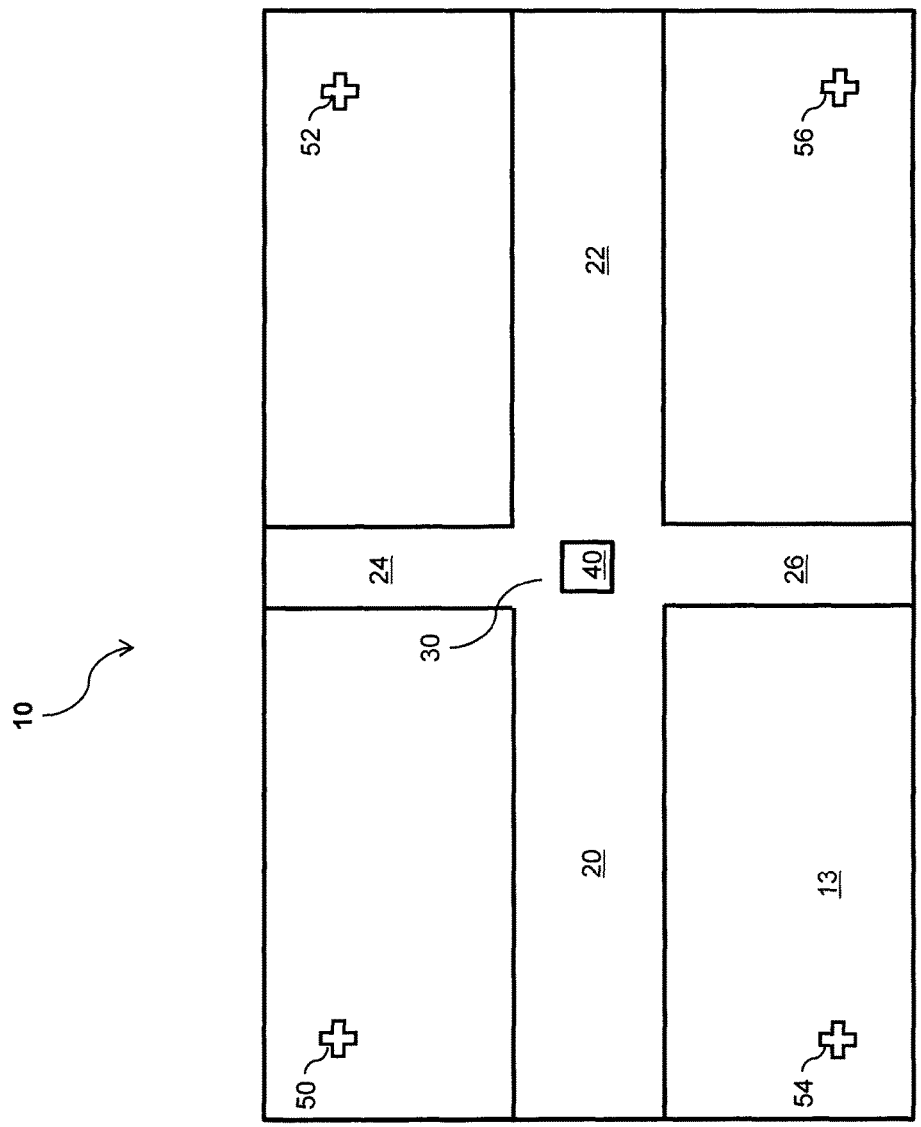
FIG. 5 is a cross-sectional view of the chip assembly of FIG. 1 with channels and a through-hole as seen along line A-A of FIG. 1, according to another non-restrictive illustrative embodiment.

Reference is now concurrently made to FIGS. 5 and 6A, which represent a cross-sectional view along line A-A of FIG. 1 and a cross-sectional elevation view of the chip assembly 10 with the channels and the through-hole 40.

For illustration purposes, four channels 20, 22, 24, 26 are represented on the inner surface 13 of the lower chip 14 of the chip assembly 10.

In contrast with the embodiment of FIG. 2, in the embodiment of FIGS. 5 and 6A, each channel (e.g. 20) extends from one extremity of the inner surface 13 of the chip (12 or 14) towards the intersecting area 30. The channels extend into the intersecting area 30, since the excitation fiber to be received in one of the channels (for example in channel 20) has a passageway 42 to be aligned with the through-hole 40 of the chip assembly 10. The passageway 42 is in fact a through-hole of the excitation fiber and is referred to as a "passageway" for the purpose of avoiding confusion of terms.

FIG. 6A illustrates a configuration where the channels (e.g. 20, 20'; 22, 22' and 24, 24') are present on the inner surface 13 of both the lower chip 14 and the upper chip 12. This configuration is used when implementing a chip assembly 10 for receiving an excitation fiber having a passageway to be aligned with the through-hole 40 of the chip assembly 10. FIG. 6B illustrates the alignment of the through-hole 40 of the chip assembly 10 with the passageway 42 of the excitation fiber 110. The excitation fiber 110 is fully engaged in channel 20, 20' and partially or totally engaged in channel 22, 22'. Channel 24, 24' is not represented on FIG. 6B for simplification purposes.

In a particular embodiment, in order to assure that the excitation fiber 110 in which the passageway 42 is bored into does not lose its guiding capability, its cladding is removed to directly access its core. Therefore, the chip material in contact with the bare excitation fiber 110 has optical characteristics similar to the cladding of the excitation fiber 110 (refractive index and transmittance). For instance, if the excitation fiber 110 is in fused silica, its refractive index is ~1.459. Thus, the chip material has a refractive index below 1.459 and has a high transmittance between 300-850 nm.

In another embodiment, the chip material is chemically inert for assuring a flow cell lifetime over several years. The flow cell needs to be cleaned regularly using solutions like sodium hypochlorite, ammoniac, ethanol etc.

In yet another embodiment, no liquid flowing through the through-hole 40 and through the passageway 42 is in contact with other (collection) fibers integrated into the flow cell, to assure flow cell integrity. This restricts the contact zone (between the excitation fiber 110 and the chip material) to few tenths of micron or less surrounding the through-hole 40 and the passageway 42.

In still another embodiment, the fluid flow is laminar when inserted into the through-hole 40 for assuring volumetric particle counts, no dead volume, or particle accumulation in dead zones.

In order to comply with the aforementioned constraints, the chip material may be a plastic having a low refractive index. An example of such a plastic is the family of Dyneon™ Fluorothermoplastics.

Rectangular channels (e.g. 20, 20'; 22, 22', etc.) are made on the upper 12 and lower 14 plastic chips for fiber positioning. The depth of the rectangular channels is a little bit less than half the diameter of the fibers used into the flow cell. The channels can be machined using conventional tools depending on plastic selection. However, due to the aforementioned low tolerances with respect to fiber versus plastic chips positioning and cost, more precise technologies like hot embossing (HE) and injection molding (IM) may be used.

Referring again to FIGS. 5, 6A and 6B, the fibers (not represented in the Figures except for the excitation fiber 110) are positioned on their respective channels (e.g. 20, 22, 24 and 26) on the lower chip 14. The excitation fiber 110 with the passageway 42 is aligned in order to have it matched with the through-hole 40 bored into the lower plastic chip 14. The through-hole 40 has a diameter substantially close to the diameter of the passageway 42. Then, the top plastic chip 12 having the same channel (e.g. 20', 22', 24', etc.) and through-hole 40 characteristics is indexed with the lower plastic chip 14. The top plastic chip 12 is aligned in order to have its through-hole 40 aligned with the passageway 42 of the excitation fiber 110.

Then, the two chips 12 and 14 are sandwiched together, and compressed using a gallery holder and a top plate (not represented in the Figures). Since the channels have a depth less than half the diameter of the fibers received in the channels, when the two plastic chips 12 and 14 are compressed, the fibers deform partially the plastic by a few tens of micron or less. This deformation holds the fibers in place and provides a sealing needed for the fluid transfer throughout the through-hole 40 and the passageway 42. The plastic material of the chips 12 and 14, because of its refractive index, acts like a cladding, maintaining the guiding capability of the excitation fiber 110 (in the case of FIGS. 5, 6A and 6B, the cladding of the excitation fiber has been removed). The mechanical characteristics (flexural modulus and hardness) of the plastic material of the chips 12 and 14 provide the sealing needed for the fluid transfer. Furthermore, the plastic material allows plastic deformation and has a certain flexibility to come into contact with the fibers along the whole channels length.

Figure 6C:
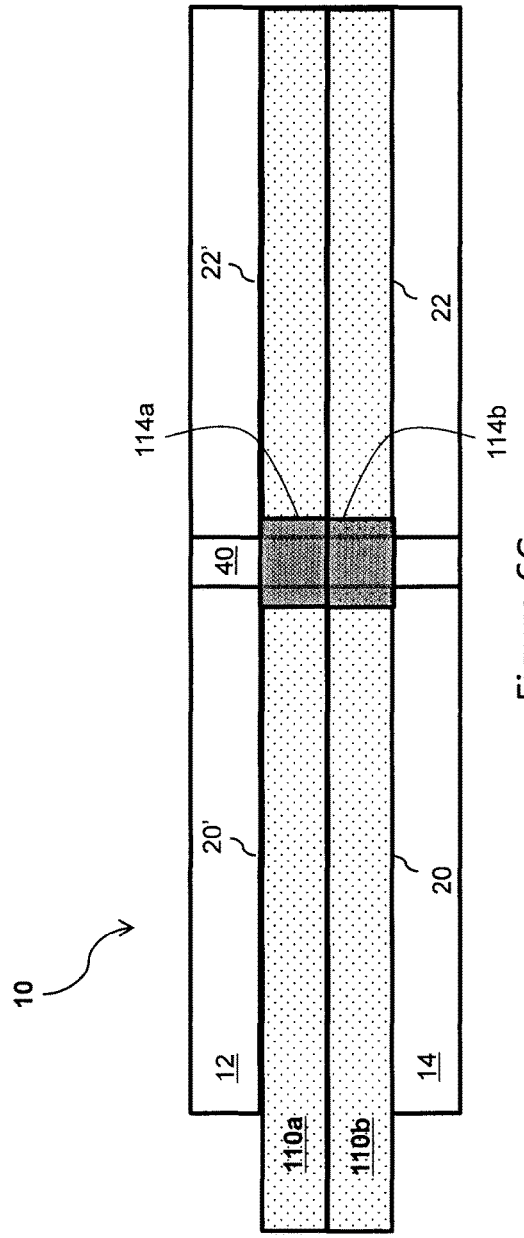
FIG. 6C is an alternate view of the chip assembly of FIG. 6A with two excitation fibers having passageways and two collection fibers, according to another non-restrictive illustrative embodiment.
Figure 6D:
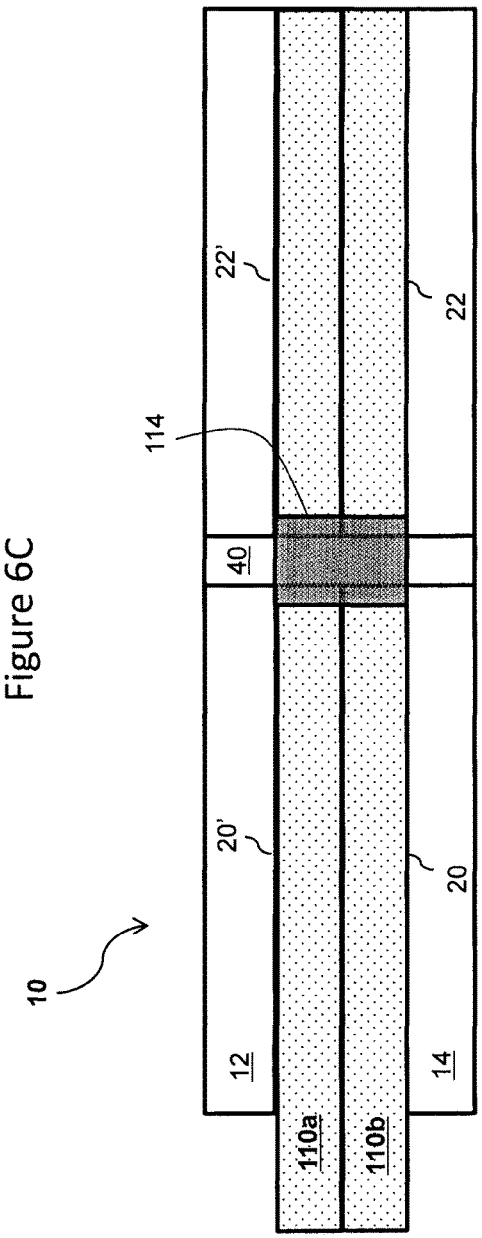
FIG. 6D is an alternate view of the chip assembly of FIG. 6A with two excitation fibers having passageways and one collection fiber, according to yet another non-restrictive illustrative embodiment.
Figure 6E:
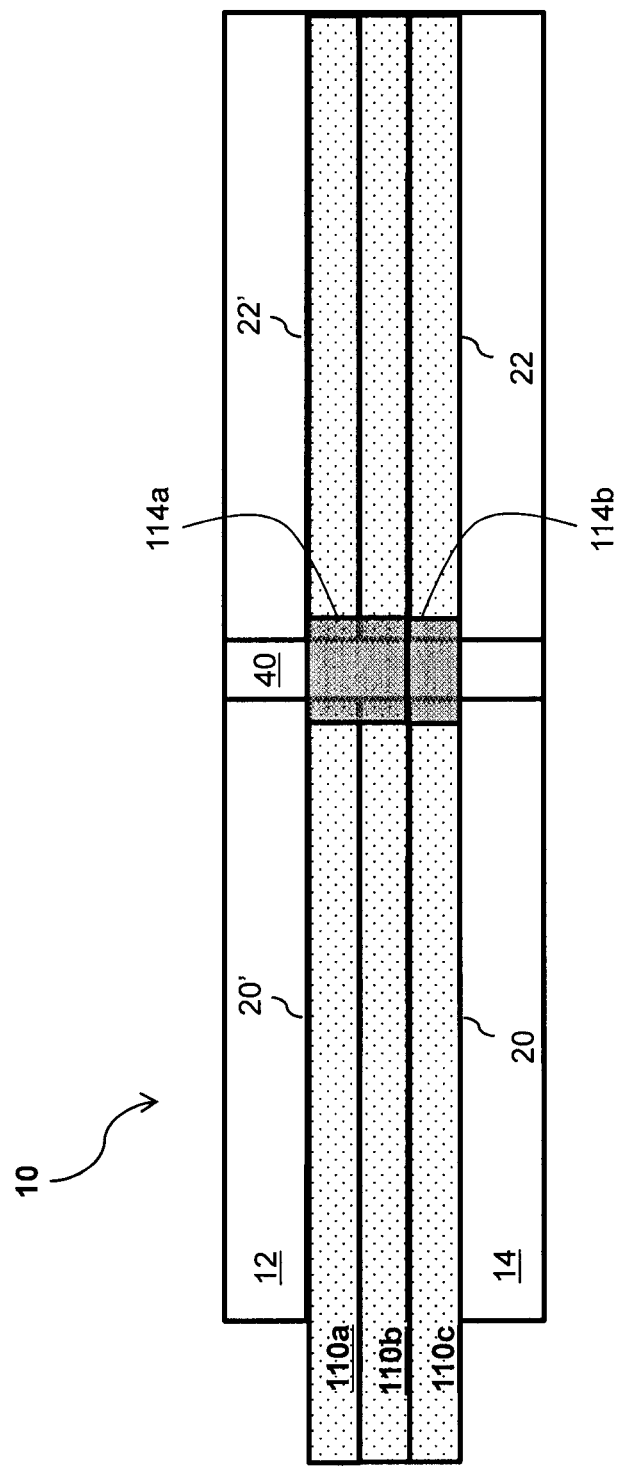
FIG. 6E is an alternate view of the chip assembly of FIG. 6A with three excitation fibers having passageways and two collection fibers, according to a further non-restrictive illustrative embodiment.

Earlier Figures suggest that one excitation fiber 110 may be inserted in channel 20 (extending into channel 22 in the chip configuration of FIGS. 5, 6A and 6B) and that collection fibers may be inserted in the channels 24 and 26, on either sides of the excitation fiber 110. However, the chip assembly 10 may be configured in multi-stage excitation and collection fiber patterns. FIGS. 6C, 6D and 6E provide alternate views of the chip assembly of FIG. 6A, with two or three excitation fibers having passageways and one or two collection fibers, according to other non-restrictive illustrative embodiments. In the variant of FIG. 6C, two (2) excitation fibers 110a and 110b are stacked on top of one another within the channels 20, 22, their passageways 42 being aligned with the through-hole 40 of the chip assembly 10 (as shown on FIG. 6B) while two collection fibers 114a and 114c are stacked on top of one another within the channel 24 (the channel 24 being shown on earlier Figures). Two more collection fibers (not shown) may be stacked on top of one another within the channel 26. The variant of FIG. 6D shows two (2) excitation fibers 110a and 110b with a common collection fiber 114 in the channel 24. The variant of FIG. 6E shows three (3) vertically stacked excitation fibers 110a, 110b and 110c and two (2) collection fibers 114a and 114b, the collection fiber 114a is common to the excitation fibers 110a and 110b while the collection fiber 114b covers the through-hole 40 within the excitation fiber 110c.

Instead of stacking two (2) excitation fibers or two (2) collection fibers, as shown on FIG. 6C, use of a dual-core excitation and/or collection fibers is also contemplated. It is also possible to stack two or more dual-core fibers, whereby for example two dual-core excitation fibers provide four (4) distinct cores for illuminating a sample solution flowing in the through-hole 40. Use of multi-core fibers is also contemplated.

The variants of FIGS. 6C, 6D and 6E, which introduce stacking of plural excitation and/or collection fibers within a single channel, can also be adapted to the configuration of the chip assembly 10 as shown in FIGS. 2, 3A and 3B. Otherwise stated, stacking of plural fibers can be applied to a configuration in which the through-hole 40 does not extend through passageways of the various excitation fibers.

Of course, the various Figures are not to scale and are intended to provide schematic illustrations of the chip assembly 10. The various channels 20, 22, 24 and 26 and the chips 12 and 14 can be sized to accommodate variable numbers of excitation fibers and collection fibers. In particular, the size of the various channels can be selected according to an overall thickness of all fibers contained within it, so that the fibers are slightly deformed when the two plastic chips 12 and 14 are sandwiched together.

Multi-stage excitation and collection fiber patterns, either using stacked fibers, dual-core fibers, multi-core fibers, or stacked dual-core or multi-core fibers, can be useful to provide excitation light at several different wavelengths. This allows to increase the number of fluorescence parameters that can be detected on the same particle passage. It is therefore possible to define a large variety of flow cell functionalities. For example in the configuration of FIG. 6C, each excitation/collection fiber pair is dedicated to a predetermined excitation wavelength. Other configurations using different numbers of excitation and collection fibers are within the scope of the present disclosure.

Flow Cell

The present disclosure also relates to a flow cell for characterizing particles in a sample solution. The present flow cell comprises the chip assembly 10.

Figure 7:
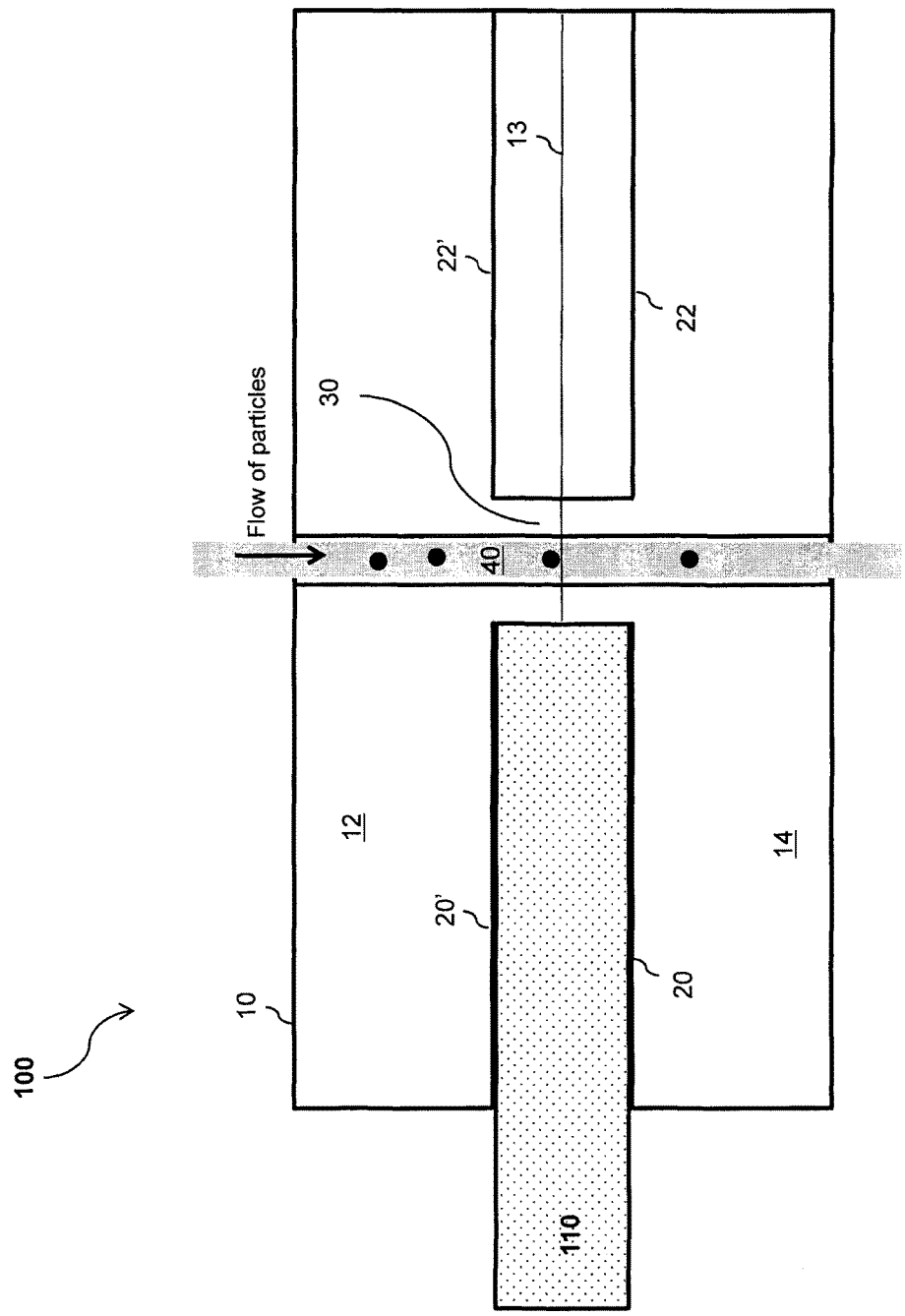
FIG. 7 is a cross-sectional elevation view of a flow cell, according to a non-restrictive illustrative embodiment.

Reference is now made to FIG. 7, which represents a cross-sectional elevation view of a flow cell 100. The flow cell 100 comprises the chip assembly 10, and more particularly the chips 12 and 14. For simplification purposes, only two channels 20, 20' and 22, 22' are represented. In the embodiment depicted in FIG. 7, the channels 20, 20' and 22, 22' are defined by both the lower chip 14 and the upper chip 12; however, the present flow cell is not limited to such a design of chip assembly and any previously discussed variant could be alternatively used. The inner surfaces 13 of the chips 12 and 14 are in contact with one another.

The chip assembly 10 composed of the chips 12 and 14 define a through-hole 40 passing through the chip assembly 10. The through-hole 40 directs a flow of particles of the sample solution through the chip assembly 10, and more particularly through the intersecting area 30. The configuration of FIG. 4 may be added above the chip 12 in order to provide hydrodynamic focusing of a sample fluid in the through-hole 40.

The flow cell 100 further comprises an excitation fiber 110 extending through the channel 20, 20' defined by the chip assembly 10. The excitation fiber 110 has a core for transporting an excitation light. In the embodiment illustrated in FIGS. 7-9, the excitation fiber 110 does not have a passageway and the chip assembly 10 is a chip assembly specifically designed to receive an excitation fiber without a passageway. The specific characteristics of the chip assembly 10 for receiving an excitation fiber 110 without a passageway have been detailed previously in the description.

The flow cell 100 also comprises at least one collection fiber extending through another one of the channels defined by the chip assembly 10. For example the excitation fiber 110 may be placed in the channel 22 and one collection fiber 114 may be placed in the channel 22', the excitation and collection fibers being co-aligned. The collection fiber collects light scattered or emitted by the particles flowing through the through-hole 40 and excited by the excitation light transported by the excitation fiber 110.

The excitation fiber and the collection fiber(s) may be made of glass, plastic or any substantially transparent guiding material. Furthermore, each fiber may have a square, rectangular, or circular cross section. As previously mentioned, the shapes of the channels of the top and base chips are adapted to accommodate the shapes of the fibers.

Figure 8:
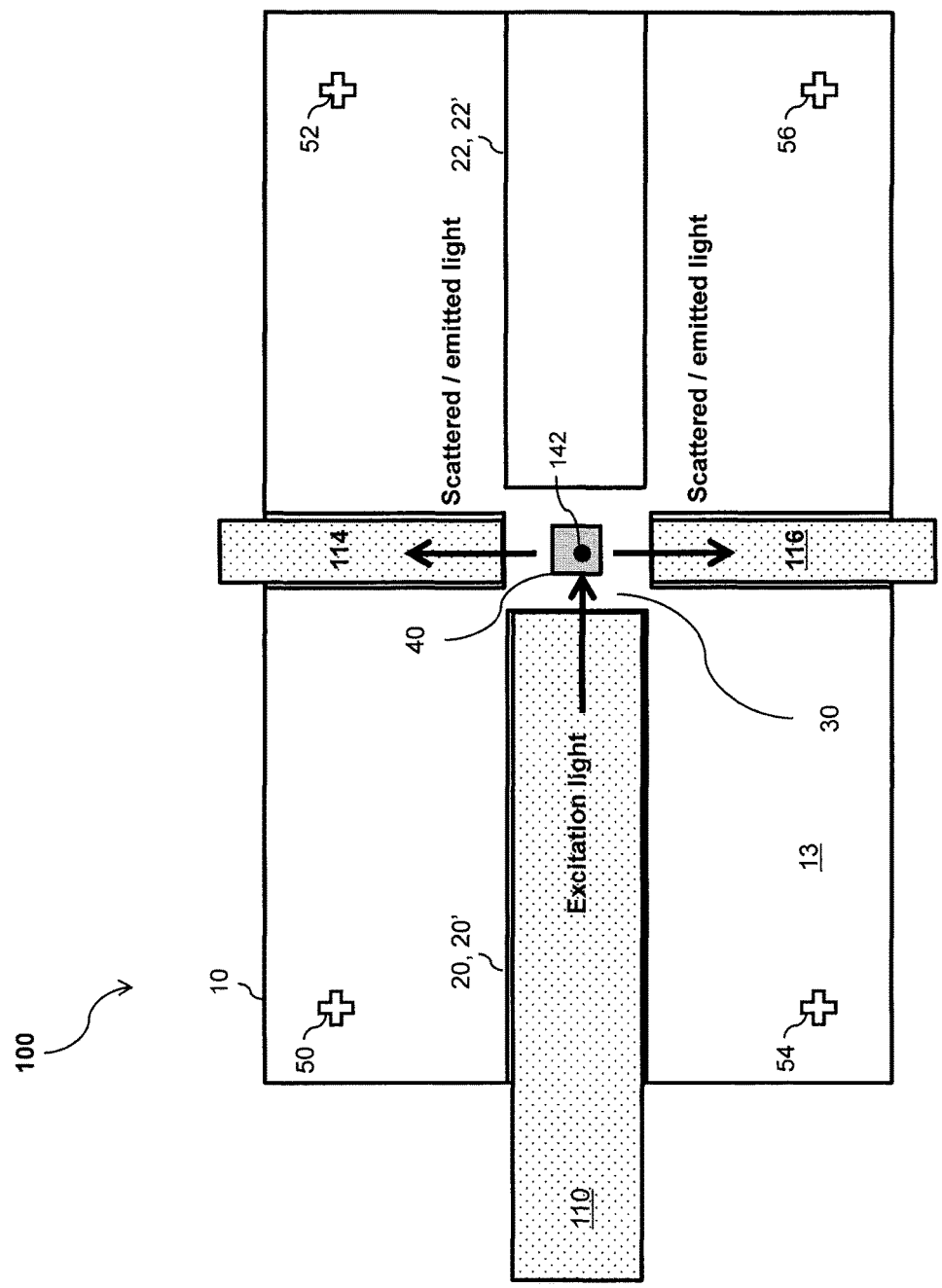
FIG. 8 is a cross-sectional top view of the flow cell of FIG. 7, according to a non-restrictive illustrative embodiment.

Reference is now made to FIG. 8, which represents a cross-sectional top view of the flow cell 100, with one excitation fiber and two collection fibers. The excitation fiber 110 generates an excitation light. A particle 142 passing through the through-hole 40 is illuminated by the excitation light. The particle 142 may scatter the excitation light and/or emit light (fluorescence), which is collected by the two collecting fibers 114 and 116. The light scattered or fluoresced by the particle 142 traverses the through-hole 40, the intersecting area 30, and a portion of the scattered and/or fluoresced light is collected by the collection fibers 114 and 116.

In FIG. 8, the flow cell 100 shows two collection fibers 114 and 116, diametrically disposed on each side of the excitation fiber 110. Alternative configurations of the excitation fiber and collecting fibers may also be implemented; for example, a single collecting fiber may be used. Use of a third collection fiber (not shown) inserted in the channel 22 is also contemplated.

Figure 9:
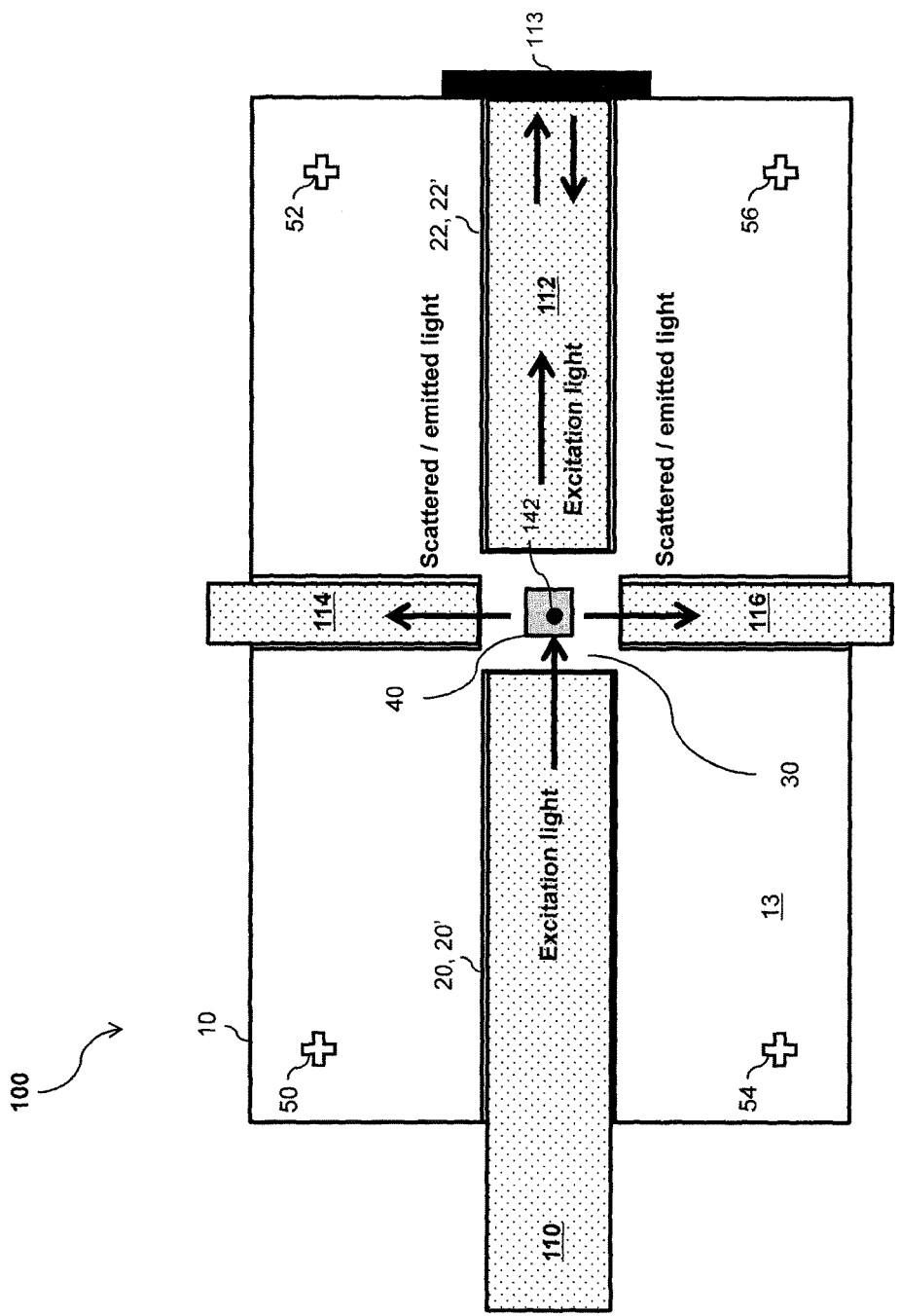
FIG. 9 is a cross-sectional top view of the flow cell of FIG. 7, according to another non-restrictive illustrative embodiment.

Reference is now made to FIG. 9, which represents a cross-sectional top view of the flow cell 100, according to an alternative embodiment. In this alternative embodiment, the flow cell 100 further comprises a reflecting fiber 112 extending through one of the channels defined by the chip assembly, opposite to the excitation fiber 110. A reflective medium 113, such as for example a mirror, a reflective surface, a metal or a dielectric coating, is affixed to the most distant end of the reflecting fiber with respect to the through-hole 40. The excitation light having passed once through the sample solution flowing through the through-hole 40 is reflected, and thereby increases the excitation light present within the excitation zone located within the through-hole 40.

Figure 10:
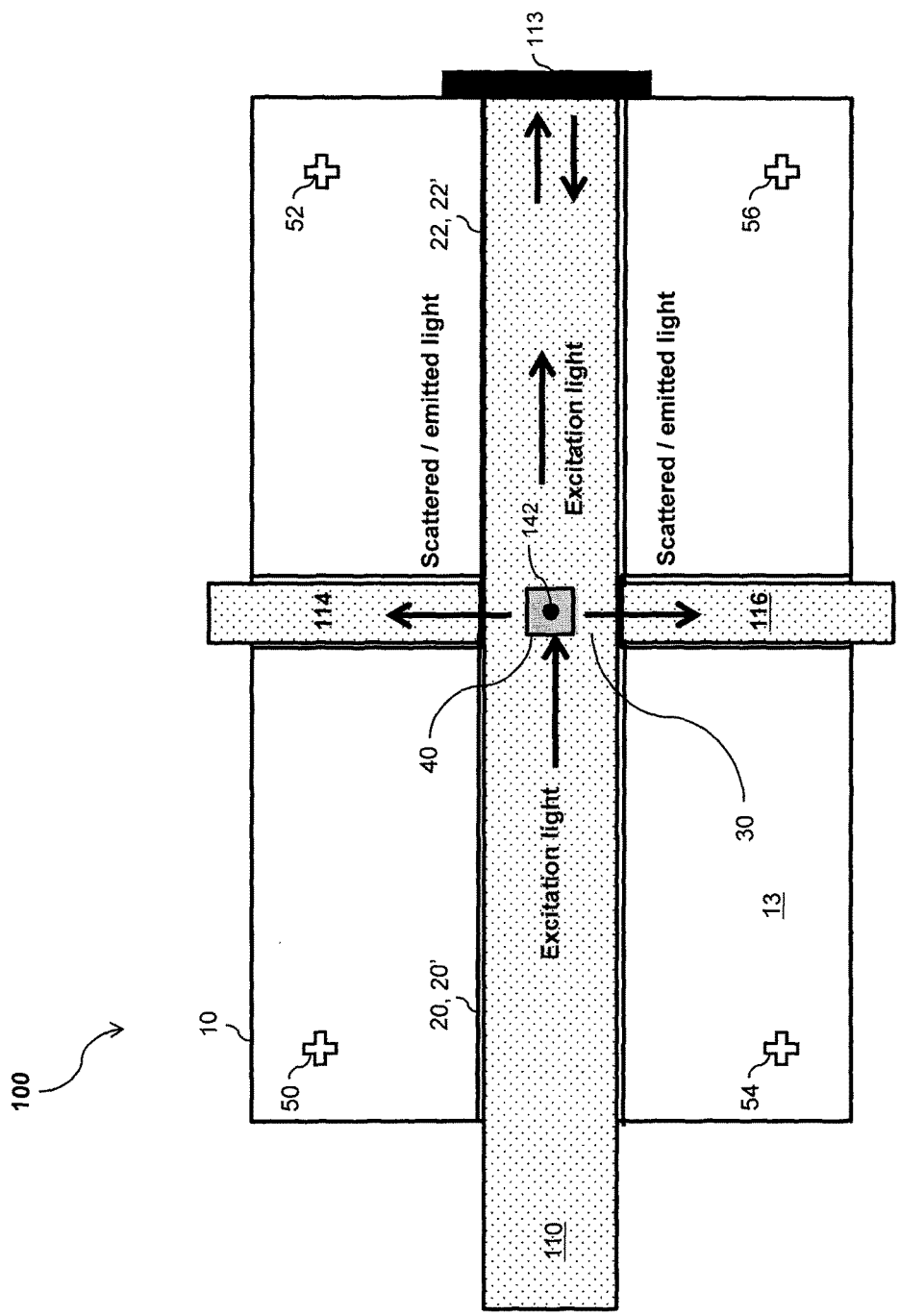
FIG. 10 is a cross-sectional top view of a flow cell, according to a non-restrictive illustrative embodiment.

Reference is now made to FIG. 10, which represents a cross-sectional top view of an alternative flow cell 100, with an excitation fiber 110 having a passageway and two collection fibers 114 and 116. In the embodiment illustrated in FIG. 10, the chip assembly 10 is a chip assembly specifically designed to receive an excitation 110 fiber with a passageway. The passageway (not explicitly represented in FIG. 10) of the excitation fiber 110 is aligned with the through-hole 40 of the chip assembly 10. The specific characteristics of the chip assembly 10 for receiving an excitation fiber 110 with a passageway have been detailed hereinabove. The excitation fiber 110 with a passageway can be extended over the channel 22, 22'. A reflective medium 113, such as for example a mirror, a reflective surface, a metal or a dielectric coating, may optionally be affixed to the most distant end of the reflecting fiber with respect to the through-hole 40. The excitation light having passed once through the sample solution flowing through the through-hole 40 is reflected, and thereby increases the excitation light present within the excitation zone located within the through-hole 40.

Figure 11:
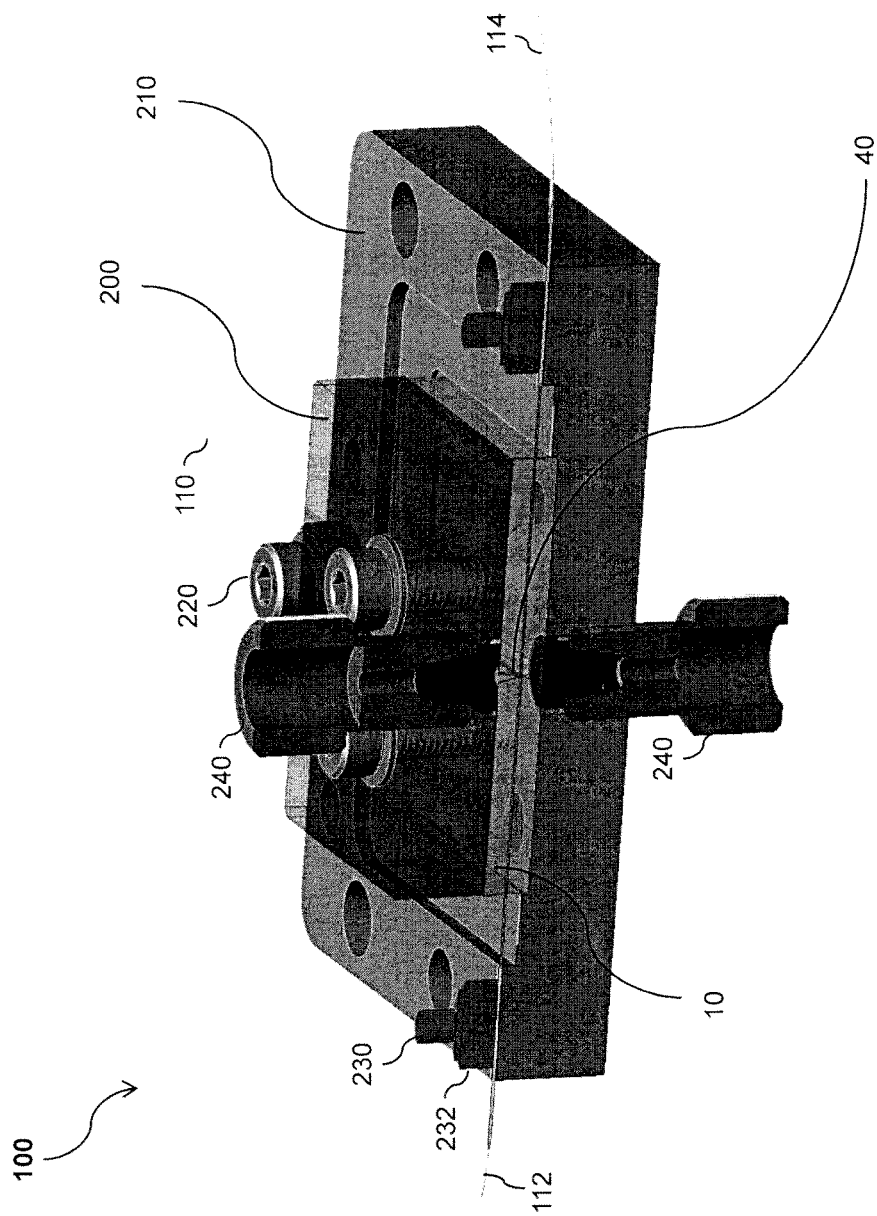
FIG. 11 is a cross-sectional perspective view of the flow cell of FIG. 7, according to still another non-restrictive illustrative embodiment.

Reference is now made to FIG. 11, which represents a cross-sectional perspective view of the flow cell 100. The flow cell 100 further comprises a gallery holder 210 and a top plate 200. The chip assembly 10 is sandwiched between the gallery holder 210 and the top plate 200. An upper surface of the chip assembly 10 is in contact with the top plate 200 and a lower surface of the chip assembly 10 is in contact with the gallery holder 210. Furthermore, appropriate securing mechanisms are used to secure the chip assembly 10 between the gallery holder 210 and the top plate 200. For instance, the securing mechanisms may consist of several screws 220 (the chip assembly may further comprise holes for receiving the screws 220). The chip assembly 10 may include the alignment guides 50-56, for inter-chip indexation. The fibers 110, 112 and 114 may be fixed to the gallery holder 210 by appropriate means, for instance soft washers 232 and screws 230.

It is possible to make a stack of a plurality of chip assemblies 10, corresponding sets of fibers 110, 112 and 114 being mounted to each chip assembly 10. The gallery holder 210 and top plate 200 respectively include a fitting 240, aligned with the through-hole 40 of the chip assembly 10 for fluid insertion/extraction. Of course, the fitting 240 is aligned with the tapering, funnel-shaped void 202 of FIG. 4, if present in a particular embodiment. Generally a tubing (plastic, stainless steel, not shown) transports the fluid from a pumping system (not shown) to the through-hole 40 and is maintained in place by the fitting 240. When a plurality of chip assemblies 10 are stacked within a single flow cell, their respective through-holes 40 are co-aligned so that fluid received at the fitting 240 can flow through the successive chip assemblies 10. If the hydrodynamic focusing configuration of FIG. 4 is used with a stack of plural chip assemblies 10, a funnel-shaped void such as 202 may be added above a topmost of the chip assemblies 10 and a symmetrical, inverted void may be added underneath a bottommost of the chip assemblies 10.

The top plate 200 participates in the sealing of the whole flow cell 100. The top plate 200 may be made of a plastic material.

The top plate 200 may be replaced by a microfluidic (μF) plate (not represented in the Figures) with a through-hole through it for fluidic transfer to the chip assembly 10 (the through-holes of the μF plate and the chip assembly 10 are aligned). The μF plate may be added or changed very easily using reversed indexation features. A top plate 200 applies pressure on the μF plate for providing sealing to the assembly comprising the μF plate and the flow cell 100 as. The μF plate may be connected to several fluidic channels; for example one channel with the sample solution and one or several channels with sheath liquid for hydrodynamic focalisation. The liquids from the channels are mixed in the through-holes of the μF plate and the chip assembly 10. For instance, the μF plate may have a network of channels that can be used for staining particles in suspension in a sample or for particle filtering before analysis in the chip assembly 10.

The flow cell 100 may further comprise multiple chip assemblies, assembled one above the other in such a manner that the pairs of chip assemblies may be secured to each other, and the through-holes of the chip assemblies are aligned to form one through-hole through the multiple chip assemblies. For example, the flow cell 100 may include two pairs of chip assemblies sandwiched between the gallery holder 210 and the top plate 200, and secured by several screws 220 therebetween. The sample solution flows through the through-hole of the first chip assembly and is analyzed according to a particular configuration of excitation fiber/collection fiber(s) having specific characteristics. The sample solution then flows through the through-hole of the second chip assembly and is analyzed according to another particular configuration of excitation fiber/collection fiber(s) having other specific characteristics. Such a configuration of multiple chip assemblies in a flow cell accommodates a greater diversity of tests, which can be performed in a more effective manner upon the same sample solution.

Although not specifically shown in FIGS. 2-11, those skilled in the art will understand that the excitation fiber(s) and the collection fiber(s) of the flow cell 100 are generally respectively coupled to light source(s) and to detection system(s) as known in the art. For instance, in one embodiment, hydrodynamic focusing is not used. Furthermore, in another embodiment, the excitation and collection fibers are configured in such a way to uniformly excite and collect light in the through-hole 40.

Flow Cytometer

Figure 12:
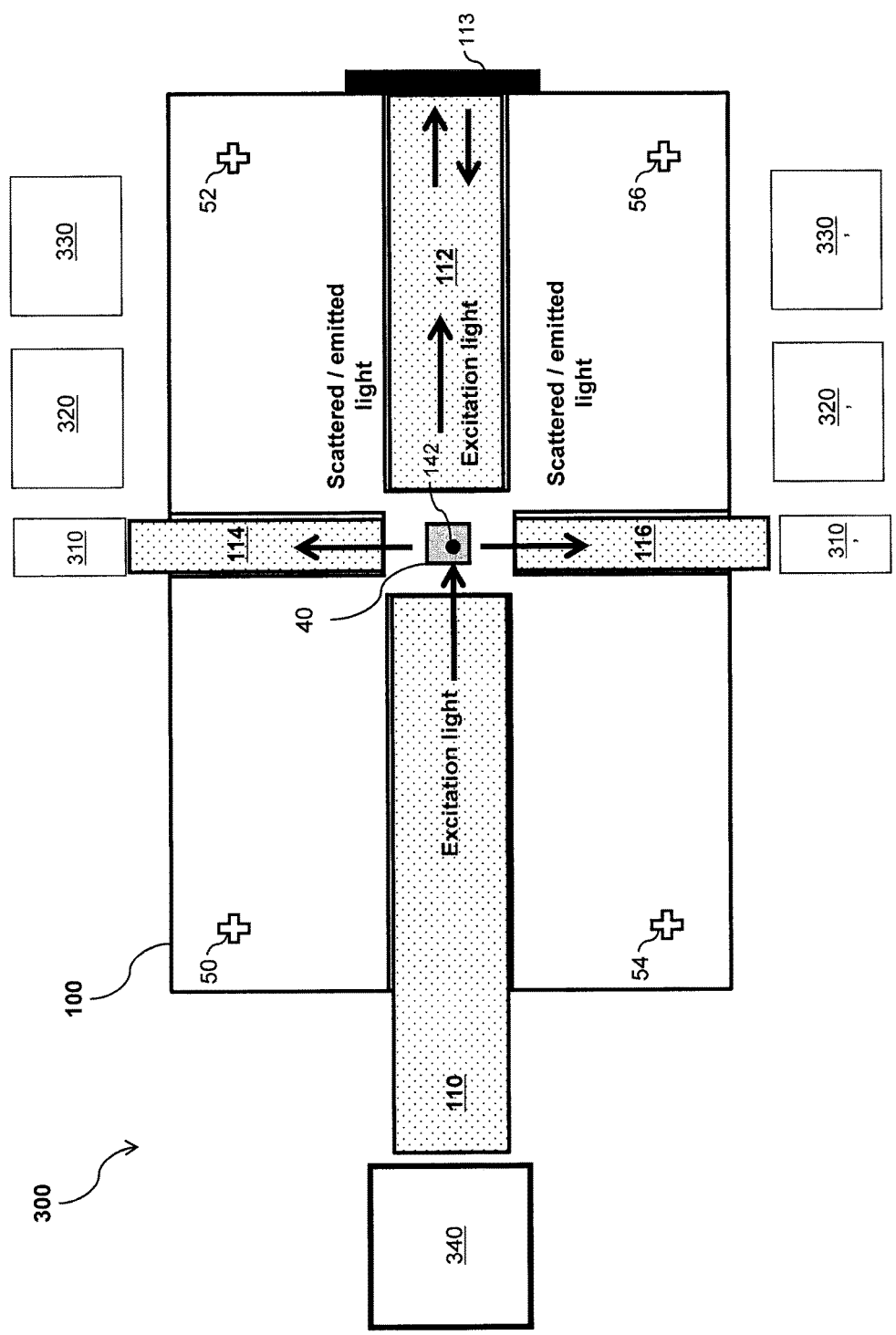
FIG. 12 is a schematic representation of a flow cytometer, according to a non-restrictive illustrative embodiment.

Reference is now made to FIG. 12, which is a schematic representation of the present flow cell 100 in an example apparatus: a flow cytometer 300. The flow cytometer 300 is used as an example only, as the present flow cell 100 can be used and implemented in various other types of apparatuses such as, for example, a cell counter.

The present flow cell 100 is thus optically connected to a light source 340. The light source 340 is connected either directly or by means of a coupling mechanism (not shown) to an extremity of the excitation fiber 110. Any means of coupling known in the art may be used such as, for example, bulk lenses, optical fiber mating connectors or mechanical or fusion splicing. Although just one light source 340 is shown in the flow cytometer of FIG. 12, the present flow cytometer is not limited to such an implementation, and may include several light sources, either operated concurrently or separately.

The light source 340 generates the excitation light to be transported by the excitation fiber 110. Examples of light sources that can be used include lasers and light-emitting diodes, typically, for example, lasers of various wavelengths such as 405, 445, 455, 473, 488, 515, 532, 560, 638 nm etc.

For illustration purposes only, the flow cell 100 comprises the excitation fiber 110 and two collection fibers 114 and 116. The collection fibers 114 and 116 collect light emitted or scattered by particles 142 flowing through the through-hole 40, in presence of excitation light. Any other configuration of the flow cell 100 and chip assembly 10 previously described may be used in the flow cytometer 300.

An excitation zone corresponds to an intersection where the excitation light (including the light reflected if a reflective surface 113 and a reflecting fiber 112 are used) and the sample solution in the through-hole 40 meet. The excitation light illuminates the excitation zone. As the sample solution flows through the through-hole 40, some of the excitation light interacts with the particle 142. The excitation light scatters upon interaction with the particle 142. If a fluorophore is used in the sample solution for cell-labeling, interaction of the excitation light with an excitable fluorophore results in light emitted in the form of fluorescence by the fluorophore at different wavelengths than the excitation light.

Depending on the requirements of the apparatus, the collection fibers 114 and 116 may further be connected to a collection optics system 310 and 310' such as for example filters and/or analog components. The collection optics system 310 and 310' may comprise collimating lenses, optical filters and dichroic mirrors to separate the scattered light from the emitted light. The collection optics system 310 and 310' are connected to one or separate optical detection systems 320, 320'. The optical detection systems 320 and 320' receive the light collected from the collection optics systems 310 and 310', if used, or directly from the collection fibers 114 and 116, if no collection optics system is used. The optical detection systems 320 and 320' transform the collected light into a corresponding electric signal. The electric signal is afterwards provided to a signal processing system 330, which determines characteristics of the particles.

Although two optical detection systems 320 and 320' are shown in FIG. 12, the present flow cytometer 300 is not limited to such an implementation. For example, one of the optical detection systems 320 could be connected to multiple optical collection systems 310 and 310', or directly to multiple collection fibers 114 and 116.

Figure 13:
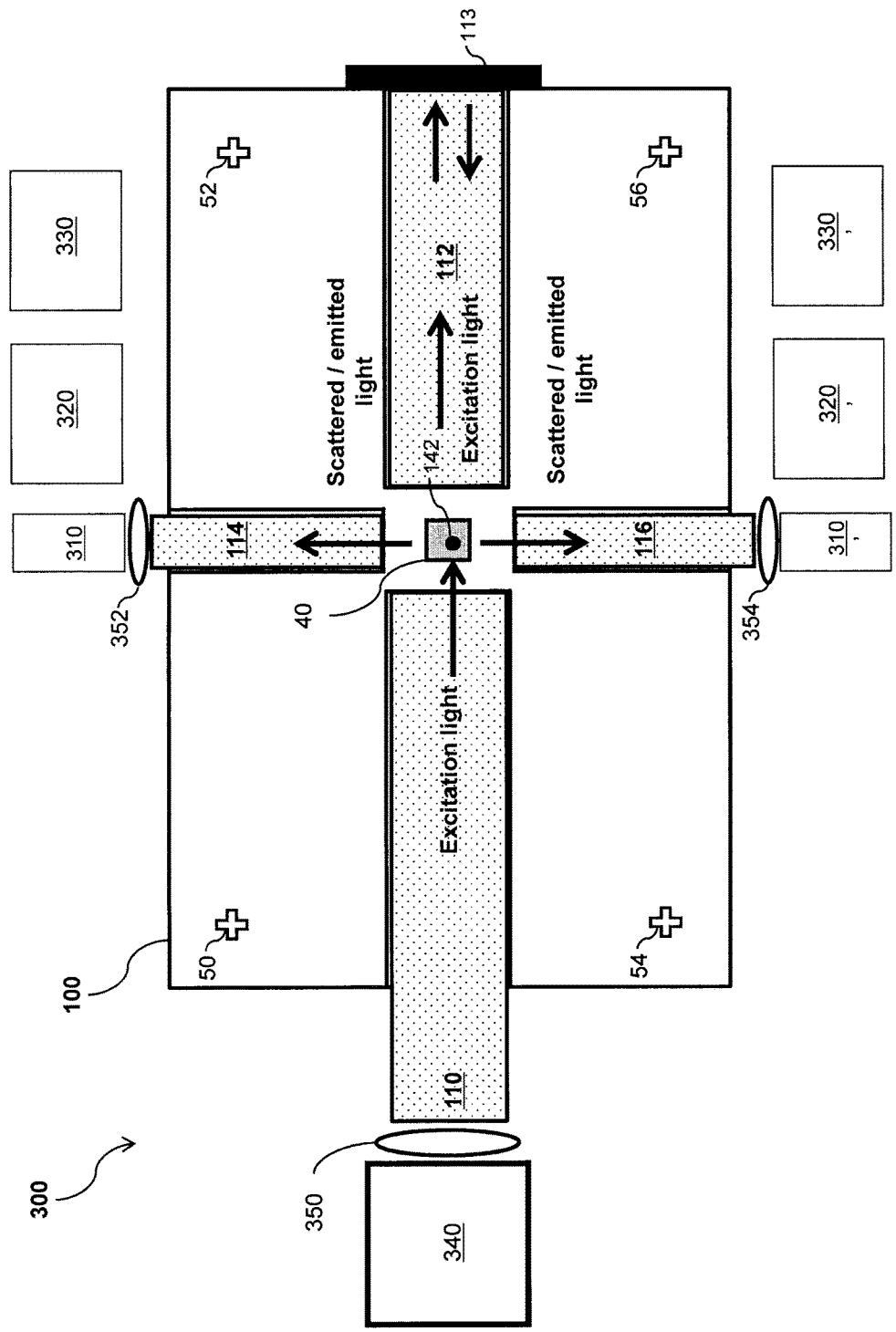
FIG. 13 is a schematic representation of a variant of the flow cytometer of FIG. 12 in which a flow cell is interchangeable.

FIG. 13 is a schematic representation of a variant of the flow cytometer of FIG. 12 in which a flow cell is interchangeable. The flow cell 100 is modified by the addition of optical lenses 350, 352 and 354. The optical lens 350 is positioned between the light source 340 and the excitation fiber 110, and focalizes the light entering the excitation fiber 110. The optical lenses 352 and 354 are positioned, respectively, between the collection fibers 114 and 116 and the collection optics systems 310 and 310'. In cases where a plurality of excitation fibers 110 and/or a plurality of collection fibers 114 or 116 are stacked within a same channel, as in the case of FIGS. 6C, 6D and 6E, or when dual-core or multi-core fibers are used, a plurality of corresponding lenses 350, 352 and 354 may be used. Using the optical lenses 350, 352 and 354, the excitation and collection fibers remain within the flow cell 100 and do not need to extend beyond it. This facilitates interchangeability of the flow cell 100 within the flow cytometer 300.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A chip assembly for use in a flow cytometer, the chip assembly comprising:
a combination of an upper chip and a lower chip, at least one of the chips defining on its inner surface at least two channels, the two channels defining therebetween a common intersecting area, each channel being adapted for receiving one or more optical fibers, and the combination of chips defining a through-hole extending throughout the chip assembly in a transverse direction relative to the channels such that the through-hole passes through the common intersecting area.

2. The chip assembly of claim 1, comprising two perpendicular pairs of channels, each pair of channels consisting of two channels aligned with each other, the two pairs of channels defining the common intersecting area.

3. The chip assembly of claim 1, wherein the chip assembly is made of plastic, the channels have a depth less than half an overall thickness of the one or more optical fibers received in the channels, and the combination of plastic chips is compressed so that the plastic is partially deformed to enable the fibers to be held in place and to provide a seal allowing for a fluid transfer by means of the through-hole.

4. The chip assembly of claim 1, wherein the chip assembly is made of glass and the common intersecting area is a parallelepiped form with all walls made of glass.

5. The chip assembly of claim 1, wherein the chip assembly has a lower chip with channels made of glass, the common intersecting area is a parallelepiped form with all walls made of glass, and an upper chip without channels made of a material having the mechanical characteristics that provide the sealing needed for fluid transfer.

6. The chip assembly of claim 1, wherein: the upper chip is replaced with a top plate comprising a funnel-shaped void positioned above the through-hole, said void tapering downwards to arrive substantially at a width of the through-hole above the level of the channels; a sheath fluid is pumped into the void and forms a stream flowing through the through-hole; and a tubing injects a sample fluid centrally within the stream of the sheath fluid to create a single file of particles suspended in the sample fluid at the center of the through-hole.

7. The chip assembly of claim 1, wherein at least one of the one or more optical fibers is a multi-core fiber.

8. The chip assembly of claim 1, wherein two or more optical fibers are stacked on top of one another within a channel.

9. A flow cell for characterizing particles in a sample solution, the flow cell comprising a chip assembly according to claim 1, and further comprising:
one or more excitation fibers extending through one of the channels defined by the chip assembly, each of the one or more excitation fibers having at least one core for transporting an excitation light; and
at least one collection fiber extending through another one of the channels defined by the chip assembly, wherein the at least one collection fiber collects light scattered or emitted by the particles flowing through the through-hole and excited by the excitation light.

10. A flow cell according to claim 9, wherein:
a single excitation fiber extends through one of the channels defined by the chip assembly, wherein the single excitation fiber has a single core for transporting an excitation light; and
a cladding of the single excitation fiber has been removed and the chip assembly is made of plastic.

11. A flow cell according to claim 9, wherein the chip assembly is made of glass.

12. A flow cell according to claim 9, wherein the chip assembly has a lower chip with channels made of glass and an upper chip without channels made of plastic.

13. The flow cell of claim 9, further comprising one or more reflecting fibers extending through one of the channels defined by the chip assembly opposite to the one or more excitation fibers, and a reflective surface at the most distant end of the one or more reflecting fibers with respect to the through-hole.

14. The flow cell of claim 9, wherein the one or more excitation fibers and the at least one collection fiber have square, rectangular, or circular cross sections, and the shape of each channel of the chip assembly is adapted for receiving its corresponding fibers.

15. A flow cytometer for characterizing particles in a sample solution, the flow cytometer comprising:
a light source for generating an excitation light; and a flow cell as defined in claim 9, wherein the at least one core of each of the one or more excitation fibers transports the excitation light.

16. The flow cytometer of claim 15; further comprising a plurality of light sources for generating excitation light at a plurality of wavelengths, wherein each of the at least one core of each of the one or more excitation fibers transports excitation light at a distinct wavelength.

17. The flow cytometer of claim 15; further comprising an optical detection system for transforming light collected by the at least one collecting fiber into a corresponding electric signal and a signal processing device for analyzing the electric signal to determine characteristics of the particles.

18. The flow cytometer of claim 15, further comprising one or more optical lenses positioned between the light source and each of the at least one core of the one or more excitation fibers.

19. The flow cytometer of claim 15, further comprising an additional optical lens positioned between each of the at least one collection fiber and collection optics connected to the optical detection system.

\* \* \* \* \*